(12) United States Patent
Pinkos et al.

(10) Patent No.: US 6,387,224 B1
(45) Date of Patent: May 14, 2002

(54) METHOD FOR DISTILLING MIXTURES CONTAINING BUTANEDIOL

(75) Inventors: Rolf Pinkos, Bad Dürkheim; Rolf Fischer, Heidelberg; Shelue Liang, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/623,109

(22) PCT Filed: Feb. 26, 1999

(86) PCT No.: PCT/EP99/01250

§ 371 Date: Aug. 29, 2000

§ 102(e) Date: Aug. 29, 2000

(87) PCT Pub. No.: WO99/44975

PCT Pub. Date: Sep. 10, 1999

(30) Foreign Application Priority Data

Mar. 5, 1998 (DE) .......................................... 198 09 493

(51) Int. Cl.[7] ............................. B01D 3/34; C07C 27/28
(52) U.S. Cl. ............................. 203/33; 203/36; 203/37; 203/71; 568/864; 568/868; 568/913
(58) Field of Search ............................. 203/36, 37, 71, 203/33, 100; 568/864, 913, 919–921, 868

(56) References Cited

U.S. PATENT DOCUMENTS

| | | | | |
|---|---|---|---|---|
| 4,200,501 A | * | 4/1980 | Panek et al. | 203/37 |
| 4,879,420 A | * | 11/1989 | Ernst | 568/617 |
| 5,342,488 A | | 8/1994 | Gosch et al. | 203/80 |
| 6,117,277 A | * | 9/2000 | Zgorzelski et al. | 203/37 |

FOREIGN PATENT DOCUMENTS

| | | |
|---|---|---|
| EP | 557 786 A1 | 9/1993 |
| JP | 09/59191 | 3/1997 |
| WO | WO 97/36846 | 10/1997 |

* cited by examiner

*Primary Examiner*—Virginia Manoharan
(74) *Attorney, Agent, or Firm*—Keil & Weinkauf

(57) ABSTRACT

A process for the separation by distillation of a mixture of 1,4-butanediol and at least one 4-hydroxybutyraldehyde, its cyclic hemiacetal and its cyclic full acetals with at least one further alcohol by carrying out the distillation in the presence of an alkaline compound. The mixture to be separated preferably contains a cyclic full acetal of 4-hydroxybutyraldehyde with a further alcohol which has a lower boiling point than butanediol and also the further alcohol in free form. The process is particularly suitable for the separation by distillation of mixtures formed in the hydrogenation of maleic acid derivatives.

6 Claims, No Drawings ated preferably comprise the latter compound.
METHOD FOR DISTILLING MIXTURES CONTAINING BUTANEDIOL The present invention relates to a process for the distillation of a mixture comprising 1,4-butanediol and 4-hydroxybutyraldehyde or its cyclic acetals.

The reaction product of the catalytic hydrogenation of maleic acid derivatives to give 1,4-butanediol generally further comprises, apart from other secondary constituents, 4-hydroxybutyraldehyde, its cyclic hemiacetal 2-hydroxytetrahydrofuran and cyclic full acetals of 4-hydroxybutyraldehyde. The cyclic acetal of 4-hydroxybutyraldehyde with 1,4-butanediol, namely 2-(4-hydroxybutoxy)tetrahydrofuran, can be separated by distillation from 1,4-butanediol only with great difficulty and is therefore a source of contaminants for the 1,4-butanediol obtained by distillation. Methods are therefore sought for reducing the content of 2-(4-hydroxybutoxy)tetrahydrofuran in the butanediol-containing hydrogenation products to be worked up.

WO 97/36846 describes a process in which crude 1,4-butanediol is subjected to a catalytic hydrogenation in the presence of from 0.5 to 5% by weight of water to reduce its 2-(4-hydroxybutoxy)tetrahydrofuran content. Such an additional hydrogenation step is complicated and considerably increases the costs of a process for isolating 1,4-butanediol. In addition, the water added has to be removed again.

JP-A 09-59191 describes a process in which 2-hydroxytetrahydrofuran is reacted with the alkyl alcohol present in crude 1,4-butanediol over a solid acid catalyst to give 2-alkoxytetrahydrofuran which is separated off by distillation. A disadvantage of this process is that 1,4-butanediol is partially cyclized to tetrahydrofuran over acid catalysts, resulting in yield losses of 1,4-butanediol. Furthermore, the butanediol acetal of 4-hydroxybutyraldehyde, whose formation is precisely to be avoided, is also formed in the presence of 1,4-butanediol. Another problem is that the alkyl alcohol derived from the dialkyl maleate is present in only a two-fold molar excess over 1,4-butanediol, added to which the latter has a higher functionality in respect of acetal formation.

It is an object of the present invention to provide a process for the distillation of the butanediol-containing crude mixtures obtained in the hydrogenation of maleic acid derivatives which gives, as distillation product, a 1,4-butanediol which is particularly low in 2-(4-hydroxybutoxy) tetrahydrofuran.

We have found that this object is achieved by a process for the separation by distillation of a mixture comprising 1,4-butanediol and at least one further compound from the group consisting of 4-hydroxybutyraldehyde, its cyclic hemiacetal and its cyclic full acetals with at least one further alcohol, which comprises carrying out the distillation in the presence of an alkaline compound.

In principle, the process of the present invention can be applied to any mixtures as long as the mixture to be separated by distillation comprises at least one of the compounds from the group consisting of 4-hydroxybutyraldehyde, its cyclic hemiacetal and its cyclic full acetals. For example, it is possible for 4-hydroxybutyraldehyde to be the only representative of the abovementioned compounds to be present. It is also possible for the open-chain aldehyde, its cyclic hemiacetal and its cyclic full acetals to be present together.

The process of the present invention is preferably used for the separation by distillation of mixtures as are obtained in the synthesis of 1,4-butanediol by catalytic hydrogenation of maleic acid derivatives. For the purposes of the present invention, maleic acid derivatives are maleic anhydride, fumaric acid, monoesters and diesters of maleic acid, monoesters and diesters of fumaric acid, succinic acid, monoesters and diesters of succinic acid and gamma-butyrolactone, as well as maleic acid itself. The maleic acid derivatives mentioned can be catalytically hydrogenated alone or as mixtures, in solvents such as water or alcohols, in the liquid phase or in the gas phase. The hydrogenation products can comprise 1,4-butanediol and also, inter alia, tetrahydrofuran, gamma-butyrolactone, alcohols such as methanol, ethanol, propanol and butanol, water and unreacted maleic acid derivatives.

In general, 4-hydroxybutyraldehyde, its cyclic hemiacetal 2-hydroxytetrahydrofuran and its cyclic full acetals are present in the mixtures obtained.

In a preferred variant of the process of the present invention, the mixture to be separated comprises cyclic full acetals of 4-hydroxybutyraldehyde with further alcohols. Preferred further alcohols are the alcohols formed as by-products in the catalytic hydrogenation of maleic acid derivatives, for example dialkyl maleates; examples of such alcohols are methanol, ethanol, n-propanol and n-butanol. Particularly preferred further alcohols are the ester alcohols which are present in bound form in the dialkyl maleates usually used as starting materials for the catalytic hydrogenation, for example methanol, ethanol, propanol and n-butanol.

The mixture to be separated preferably comprises cyclic full acetals of 4-hydroxybutyraldehyde with further alcohols which have a lower boiling point than 1,4-butanediol. Examples are methanol, ethanol, propanol and n-butanol.

In a particularly preferred variant of the process of the present invention, the further alcohol present in bound form in the cyclic full acetal of 4-hydroxybutyraldehyde is also present in free form in the mixture to be separated. Examples are mixtures in which 2-methoxytetrahydrofuran or 2-ethoxytetrahydrofuran are present in addition to methanol or ethanol, respectively. Such mixtures are obtained, for example, in the hydrogenation of dimethyl or diethyl maleates.

The mixtures to be separated can further comprise 2-(4-hydroxybutoxy)tetrahydrofuran. The mixtures to be separated preferably comprise the latter compound.

In a very particularly preferred variant of the process of the present invention, the mixtures to be separated comprise 2-(4-hydroxybutoxy)tetrahydrofuran and also 2-methoxytetrahydrofuran or 2-ethoxytetrahydrofuran plus methanol or ethanol, especially when dimethyl or diethyl maleate has been hydrogenated.

The distillation of the mixture to be separated is carried out in the presence of alkaline compounds. For the purposes of the present invention, alkaline means that the compound counters the protonation of the alcohols, aldehydes, hemiacetals and full acetals present in the mixture concerned and thus reduces the concentration of the corresponding protonated species. Soluble or insoluble alkaline compounds can be used in the mixture to be separated. Preference is given to using soluble alkaline compounds in the mixture to be separated. Preferred alkaline compounds are ammonia, amines, alkali metal compounds or alkaline earth metal compounds, preferably the oxides, hydroxides, carbonates, alkoxides such as methoxides, ethoxides, propoxides and butoxides, and carboxylates such as formates, acetates and propionates, in each case of lithium, sodium, potassium magnesium and calcium.

In general, the concentration of the alkaline compound in the mixture to be distilled is, averaged over time, from 0.0001 to 5 percent be weight, preferably from 0.001 to 1 percent by weight, particularly preferably from 0.01 to 0.5 percent by weight.

The alkaline component can be added in undiluted form or as a solution in solvent, for example water or alcohol. The alkaline component is preferably added as an aqueous, aqueous-alcoholic or alcoholic solution. If the process of the present invention is used for working up hydrogenation products from the synthesis of 1,4-butanediol, the addition is generally carried out after the hydrogenation step.

The distillation can be carried out in one or more stages, for example in one or more distillation columns, and can be carried out continuously or batchwise. The distillation is preferably carried out continuously in two or more stages. If the mixture to be distilled comprises, in addition to 1,4-butanediol, a further alcohol having a lower boiling point, as is generally the case in the hydrogenation products from the synthesis of 1,4-butanediol, the distillation is advantageously carried out in at least two stages, where the further alcohol is distilled off in a first stage and 1,4-butanediol is distilled off in a second stage. The distillation can also be carried out in more than two stages. For example, low boilers such as methanol or ethanol or tetrahydrofuran can be separated off in a first stage, intermediate boilers such as butyrolactone and diesters of succinic acid can be taken off in a second stage and 1,4-butanediol can be separated from high boilers such as butanediol succinate in a third stage. If the distillation is carried out in a plurality of stages, it is also possible to add the alkaline compound, at least in part, only after the low boilers have been separated off. The high-boiling fraction remaining as bottoms after the last distillation stage, in which the alkaline compound is present, can be recycled to the first distillation stage.

The process of the present invention gives very pure 1,4-butanediol. In the distillation of the butanediol-containing reaction product from the hydrogenation of dialcyl maleate, 2-(4-hydroxybutoxy)tetrahydrofuran contents of less than 2000 ppm, preferably less than 1000 ppm, particularly preferably less than 500 ppm, are achieved.

The invention is illustrated by the following examples.

As mixture to be separated by distillation, use is made of the reaction product from the gas-phase hydrogenation of dimethyl maleate over a Cu/Mn/Al catalyst (T 4489 from Süd-Chemie AG, Munich, Germany) at 60 bar at 190° C. The hydrogenation product comprises about 51% by weight of 1,4-butanediol, 41% by weight of methanol, about 0.05% by weight of 2-methoxytetrahydrofuran, about 0.05% by weight of 2-hydroxytetrahydrofuran, about 0.05% by weight of 2-(4-hydroxybutoxy)tetrahydrofuran plus 1% by weight of tetrahydrofuran, 3% by weight of gamma-butyrolactone, 1% by weight of butanol and 1% by weight of water. The reaction product was separated in the example according to the present invention and in the comparative example.

EXAMPLE 0.8 g of KOH are dissolved in 745 g of the reaction product. Subsequently, predominantly methanol and tetrahydrofuran are distilled off at atmospheric pressure. The remaining mixture is then fractionally distilled by means of a packed column with runback divider (reflux ratio=10) at 40 mbar. At a temperature at the bottom of 146° C. and a temperature at the top of 136° C., 1,4-butanediol having a 2-(4-hydroxybutoxy)tetrahydrofuran content of from 300 to 400 ppm is obtained at the top of the column.

COMPARATIVE EXAMPLE

The procedure of the example according to the present invention is repeated without addition of KOH. The 2-(4-hydroxybutoxy)tetrahydrofuran content of the 1,4-butanediol obtained is from 900 to 1000 ppm.

We claim:

1. A process for the separation by distillation of 1,4-butanediol from a mixture obtained in the catalytic hydrogenation of maleic acid derivatives, said mixture comprising 1,4-butanediol and at least one further compound selected from the group consisting of 4-hydroxybutyraldehyde, its cyclic hemiacetal and its cyclic full acetals with at least one further alcohol, wherein the distillation is carried out in the presence of an alkaline compound and a 1,4-butanediol whereby a reduced 2-(4-hydroxybutoxy) tetrahydrofuran content is obtained.

2. A process a claimed in claim 1, wherein the mixture to be separated comprises a cyclic full acetal of 4-hydroxybutyraldehyde and at least one further alcohol which has a lower boiling point than butanediol.

3. A process as claimed in claim 2, wherein the at least one further alcohol is additionally present in free form is the mixture to be separated.

4. A process as claimed in claim 3, wherein, at least two distillation stages, the at least one further alcohol is distilled off in a first stage and butanediol is distilled off in a second stage.

5. A process as claimed in claim 1, wherein the alkaline compound is soluble in the mixture to be separated.

6. A process as claimed in claim 1, wherein the alkaline compound is selected from the group consisting of oxides, hydroxides, carbonates, carboxylates and alkoxides of lithium sodium, potassium, magnesium and calcium.

* * * * *